United States Patent [19]
Yagi et al.

[11] Patent Number: 6,159,999
[45] Date of Patent: Dec. 12, 2000

[54] ANTIMICROBIAL AND ANTISEPTIC METHODS USING ANTIMICROBIAL COMPOSITION

[75] Inventors: Minoru Yagi; Tetsuya Aoki, both of Tokyo, Japan

[73] Assignee: Kurita Water Industries Ltd., Tokyo, Japan

[21] Appl. No.: 09/216,726

[22] Filed: Dec. 21, 1998

[30] Foreign Application Priority Data

Dec. 22, 1997 [JP] Japan ..................... 9-353181

[51] Int. Cl.[7] .................. A61K 31/425; A61K 31/19; A61K 31/045
[52] U.S. Cl. ................... 514/372; 514/557; 514/728; 514/747; 514/844; 514/846; 514/848
[58] Field of Search ................... 514/372, 557, 514/728, 747, 844, 846, 848

[56] References Cited

U.S. PATENT DOCUMENTS

| | | | |
|---|---|---|---|
| 5,025,069 | 6/1991 | Deguchi et al. | 252/174.17 |
| 5,091,400 | 2/1992 | Yagi et al. | 514/372 |
| 5,523,020 | 6/1996 | Yagi et al. | 252/404 |
| 5,534,487 | 7/1996 | Gironda | 504/290 |
| 5,559,083 | 9/1996 | Kubota et al. | 504/269 |
| 5,716,625 | 2/1998 | Hahn et al. | 424/401 |
| 5,728,662 | 3/1998 | Vlasblom | 510/130 |

FOREIGN PATENT DOCUMENTS

| | | |
|---|---|---|
| 2 201 673 | 9/1988 | European Pat. Off. . |
| 0 300 483 | 1/1989 | European Pat. Off. . |
| 0 326 262 | 8/1989 | European Pat. Off. . |
| 0 332 336 | 9/1989 | European Pat. Off. . |
| 0 435 439 | 7/1991 | European Pat. Off. . |
| 0 648 415 | 4/1995 | European Pat. Off. . |
| 0 816 349 | 1/1998 | European Pat. Off. . |
| 1-190602 | 7/1989 | Japan . |
| 1-316301 | 12/1989 | Japan . |
| 2-57046 | 12/1990 | Japan . |
| 7-69816 | 3/1995 | Japan . |
| 7-101890 | 4/1995 | Japan . |
| 7-330520 | 12/1995 | Japan . |
| 8-259410 | 10/1996 | Japan . |

OTHER PUBLICATIONS

Database WPI, Section ch, week 9343, Derwent Publications Ltd., London, GB, class C02, AN 93–339711, XP002099351 & JP 05 247011A (Pachem Asia KK), Sep. 24, 1993.

Database WPI, Section ch, week 9608, Derwent Publications Ltd., London GB, class C03, AN96–074695, XP002099352 & JP07 330520A (Kurita Water Ind Ltd), Dec. 19, 1995.

Database WPI, Section ch, week 9204, Derwent Publications Ltd., London, GB, class C02, An92–030653, XP002099353 & JP03279373 A (Kurita Water Ind Ltd), Dec. 10, 1991.

Database WPI, Sectin ch, week 9828, Derwent Publications Ltd., London GB, class A97, An 98–316747, XP002099354 & Jp10 114761A (Takeda Chem Ind Ltd), May 6, 1998.

*Primary Examiner*—Kevin E. Weddington
*Attorney, Agent, or Firm*—Kanesaka & Takeuchi

[57] ABSTRACT

An antimicrobial composition is provided in which the skin irritation of isothiazolone type compound is decreased and the injection operation properties thereof is improved by forming it as an uniform solution. The composition contains isothiazolone type compound and a compound which decreases the skin irritation of the former in a molar ratio of 1:0.1–50 and is dissolved in a solvent.

40 Claims, No Drawings

ANTIMICROBIAL AND ANTISEPTIC METHODS USING ANTIMICROBIAL COMPOSITION

FIELD OF THE INVENTION AND RELATED ART STATEMENT

The present invention relates to methods of using an antimicrobial composition and, in particular, to a novel antimicrobial composition in which the skin irritation of the isothiazolone type compounds such as 5-chloro-2-methyl-4-isothiazoline-3-one (hereafter referred to as Cl-MIT) is decreased and the handling properties thereof are improved by means of forming it in the solution form.

The isothiazolone type compounds represented by Cl-MIT having following formula have been widely used as slime control agent, bacteriocide, algicide, and fungicide for various systems such as cooling water system, paper mill system, paint, adhesive, cutting fluid, and night soil treatment system.

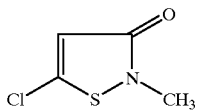

(I)

However, the isothiazolone type compounds are known for its highly irritating nature to skin and consequently, great care was required in the handling of chemicals which include these compounds in the composition.

As a means of solving these problems, it is proposed to form a solid form molecular compound (a compound in which two or more stable molecules combine with each other with an inter-molecular force such as hydrogen bond or van der Waals force, in which specific form includes clathrate compound and complex) from the isothiazolone type compound, by means of carboxylic acid, phenol, alcohol, amide type compound so that the skin irritation of isothiazolone type compounds is decreased and that its stability is improved (Japanese patent applications JP 2-57046B, and JP 1-190602A, JP 7-69816A, JP 7-101890A, and JP 7-330520A).

The forms in which the molecular compound is employed include using the molecular compound in powder form, or using the molecular compound powder after being formed in tablets. In addition, it is proposed, for the purpose of improving the ease of control and operation properties at the addition of chemical, to disperse the molecular compound in dispersion media such as water or organic solvents, making it a liquid chemical (JP 1-31630A and JP 8-259410A).

However, the liquid chemical comprising the aforementioned molecular compound had several problems such as: although the molecular compound is dispersed into fine particles, the uniformity is not sufficient to prevent clogging an injection pump or piping; it tends to solidify when cares are not taken to prevent it from drying; a special type pump is required to inject it due to its high viscosity because a viscosity improver is usually added to it to prevent particles from sedimentation.

Therefore, a chemical having a decreased skin irritation and improved stability as well as an uniformity to enable an excellent injection operation properties has been needed.

OBJECT AND SUMMARY OF THE INVENTION

It is an object of the present invention to provide an antimicrobial composition which overcomes the problems of the prior art as pointed out in the above, suppressing the skin irritation of the isothiazolone type compounds and improving the stability of the same, while improving the injection operation properties and stability in storage by means of forming the composition in the form of uniform solution.

An antimicrobial composition of the present invention contains one or more isothiazolone type compounds and a compound which can decrease the skin irritation of the isothiazolone type compounds in a molar ratio of 1:0.1–1:50, and preferably 1:0.5–1:20, and is dissolved in a solvent.

In the antimicrobial composition of the present invention, the compound which can decrease the skin irritation of the isothiazolone type compounds (hereafter it may be referred to as "skin irritation suppressor") is supposed to suppress the skin irritation by combining itself with the isothiazolone type compounds to form a molecular compound.

This molecular compound shows a more drastic decrease in skin irritation in the solution state. The reason for this is supposed to be that the isothiazolone type compounds and the skin irritation suppressor have a relatively strong inter-molecular bond in the solution state and that the skin irritation suppressor masks the skin irritating portion in the structure of the isothiazolone type compounds to effect a decrease in skin irritation.

In addition, since the antimicrobial composition of the present invention is in the solution state, the aforementioned problems in injecting a dispersion liquid are overcome and the stability in storage is also greatly improved.

DETAILED DESCRIPTION OF THE PREFERRED EMBODIMENTS

In the present invention, as the compounds which can decrease the skin irritation of the isothiazolone type compounds, dicarboxylic acids, aromatic carboxylic acids, phenolic compounds, alcoholic compounds and amide compounds are preferred.

Isothiazolone type compounds related to the present invention include one or more compounds represented by the following general formulas:

(1)

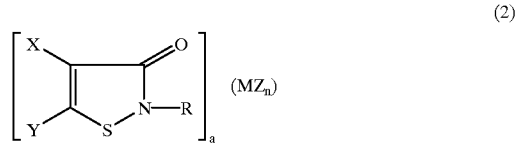

(2)

(In the formulas (1) and (2) shown above, R, X, M, Z, a, and n represent the followings, respectively:

R: Hydrogen atom, alkyl group, alkenyl group, alkynyl group, or aralkyl group;

X: Hydrogen atom or halogen atom;

Y: Hydrogen atom or halogen atom;

(X and Y may condense to form a benzene ring)

M: Cationic atom or group selected from a group consisting of alkali metals, alkali earth metals, heavy metals, and amine;

Z: Anion atom or group having a solubility sufficiently high to form a complex with the cation M;

a: An integral number 1 or 2; and n: An integral number with which the anion Z fills the valence of the cation M.)

The isothiazolone type compounds include, for instance, such compounds represented by the structural formula (1) in the above as 5-chloro-2-methyl-4-isothiazoline-3-one (Cl-MIT); 2-methyl-4-isothiazoline-3-one; 4,5-dichloro-2-methyl-4-isothiazoline-3-one; 2-ethyl-4-isothiazoline-3-one; 2-octyl-4-isothiazoline-3-one; 5-chloro-2-octyl-4-isothiazoline-3-one; 4,5-dichloro-2-octyl-4-isothiazoline-3-one; 1,2-benzo-isothiazoline-3-one; and complex of these compounds with such salts as magnesium chloride, magnesium nitrate, copper chloride, copper nitrate, and calcium chloride. In the present invention, however, the isothiazolone type compounds which do not form complex with salts as shown in the formula (1) are preferred since they form molecular compounds more easily with the skin irritation suppressors in the solution and have a higher degree of skin irritation suppression.

On the other hand, the compounds which decrease the skin irritation of the isothiazolone type compounds include dicarboxylic acids, aromatic dicarboxylic acids, phenolic compounds, alcoholic compounds, and amide compounds. There is no limitation in the skin irritation suppressor as far as it can decrease the skin irritation of the isothiazolone type compounds but it is preferable to use one or more of the compounds in the following, which are confirmed to form a crystalline molecular compounds with the isothiazolone type compounds, since they will form a strong intermolecular bond also in the solution state.

I. Carboxylic acids: dicarboxylic acids of the following general formula (3) or aromatic carboxylic acids of the following general formula (4):

HOOC—R$^1$—COOH  (3)

(In the formula (3), R$^1$ represents single bond, alkylen group with 1–4 carbon atoms, alkenylene group with 1–4 carbon atoms, or alkynylene group with 1–4 carbon atoms.)

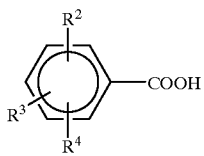

(4)

(In the formula (4), R$^2$, R$^3$, and R$^4$ are independent from each other and represent hydrogen, halogen, carboxyl group, hydroxyl group, nitro group, amino group, amide group, and carboxylic anhydride group, as well as alkyl group, alkenyl group, alkynyl group, alkoxy group, alkanone group, or alkanal group each with 1–3 carbon atoms.)

Specifically, the compounds represented by the general formula (3) include such compounds as oxalic acid, malonic acid, succinic acid, fumaric acid, maleic acid, and acetylenedicarbonic acid. The compounds represented by the general formula (4) include such compounds as benzoic acid; phthalic acid; trimellitic acid; pyromellitic acid; 4-nitrobenzoic acid; 4-chloro-3-nitrobenzoic acid; 2-chloro-4-nitrobenzoic acid; 4-chloro-2-nitrobenzoic acid; 2,4-dinitrobenzoic acid; 4-nitrophthallic acid; 3,5-diiodosalicylic acid; 3,5-dinitrosalicylic acid; genticinic acid (2,5-dihydroxybenzoic acid); and protocatechuic acid (3,4-dihydroxybenzoic acid).

As carboxylic acids other than those cited above, deoxycholic acid and the like can be also included.

II. Phenolic compounds: compounds represented by the following formulas (5), (6), or (7):

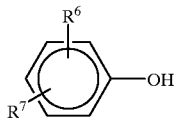

(5)

(In the formula (5), R$^6$ and R$^7$ represent alkyl group with 1–4 carbon atoms.)

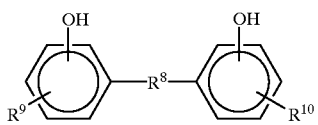

(6)

(In the formula (6), R$^8$ represents methylene group, alkylidene group with 2–4 carbon atoms, cyclohexylidene group, S atom, or SO$_2$ group, and R$^9$, R$^{10}$ represent hydrogen atom or halogen atom.)

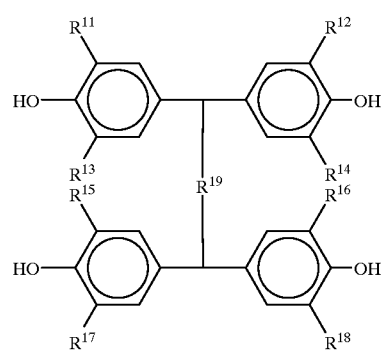

(7)

(In the formula (7), R$^{11}$–R$^{18}$ represent hydrogen atom, alkyl or alkoxy group with 1–3 carbon atoms, or halogen atom, and R$^{19}$ represents single bond, methylene group, ethylene group, or phenylene group.)

Specifically, the compounds represented by the general formula (5) include 2,4-di-t-butylphenol; 2,4-dipropylphenol; and the like.

The compounds represented by the general formula (6) include 2,2'-methylene-bis(4-chlorophenol); 2,2'-thio-bis(4-chlorophenol); 4,4-cyclohexylidenebisphenol; 4,4'-ethylidenebisphenol; 4,4'-isobutylidenebisphenol; and the like.

The compounds represented by the general formula (7) include 1,1,2,2-tetrakis(4-hydroxyphenyl)ethane; 1,1,2,2-tetrakis(3-methyl-4-hydroxyphenyl)ethane; 1,1,2,2-tetrakis(3-chloro-4-hydroxyphenyl)ethane; and the like.

As phenolic compounds other than those cited above, 2,5-di-t-butylhydroquinone; t-butylhydroquinone; 2,5-bis(2,4-dimethylphenyl)hydroquinone; 2,4-dihydroxybenzophenone; 4,4'-dihydroxybenzophenone; 2,2', 4,4'-tetrahydroxybenzophenone; 2-hydroxy-4-methoxybenzophenone; 1,1'-bi-2-naphtol and the like can be also included.

III. Alcoholic Compounds:

Specifically, such compounds as 1,1,6,6-tetraphenyl-2,4-hexadiyne-1,6-diol; 1,6-bis(2-chlorophenyl)-1,6-diphenyl- 2,4-hexadiyne-1,6-diol; 1,1-di(2,4-dimethylphenyl)-2-propyne-1-ol; 1,1,4,4-tetraphenyl-2-butyne-1,4-diol; 1,1,2,2,-tetraphenylethane-1,2-diol; 1,1,6,6-tetra(2,4-dimethylphenyl)-2,4-hexadiyne-1,6-diol; 9,10-diphenyl-9,10-dihydroxyanthrathene; 9,10-di(4-methylphenyl)-9,10-dihydroxyanthrathene; α, α, α', α'-tetraphenyl-1,1'-biphenyl-2,2'-dimethanol; and cyclodextrins are included.

IV. Amide Compounds:

Specifically, diphenic bis(dicyclohexylamide) and the like are included.

There is no limitation in the solvent used in the present invention, as far as it can dissolve the isothiazolone type compounds and the skin irritation suppressors, but since the systems to which the present invention is applied are mostly water system, water or hydrophilic solvents are preferable considering the solubility or dispensability of the effective components. The hydrophilic solvents used in the present invention include amides such as dimethylformamide, glycols such as ethyleneglycol, propyleneglycol, diethyleneglycol, and dipropyleneglycol, glycolesters such as methylcellosolve (ethyleneglycol monomethylether), phenylcellosolve, diethyleneglycol monomethylether, and dipropyleneglycol monomethylether, alcohols with carbon atoms up to 8, and esters such as methyl acetate, ethylacetate, 3-methoxydibutyl acetate, 2-ethoxymethyl acetate, 2-ethoxyethyl acetate, and propylene carbonate, and the lie. These solvents can be used singly or in mixture of two or more solvents.

In the present invention, the concentration of the isothiazolone type compounds in the solution is preferably from 0.1 to 5% by weight in terms of practice. The skin irritation suppressor is used in a molar ratio to the isothiazolone type compounds of 1:0.1–1:50, and preferably 1:0.5–1:20, the number 1 being for the isothiazolone type compounds. The concentration of the skin irritation suppressor in the solution is preferably 0.1–20% by weight.

In the present invention, in order to add other functions to the antimicrobial composition, the following additives under (a)–(e) can be combined.

(a) Corrosion inhibitor: For example, tolyltriazole, benzotriazole, methylbenzotriazole, molybdic acid, tungstic acid, silicic acid, nitrous acid, 2-phosphonobutane-1,2,4-tricarbonic acid, hydroxyethylidenediphosphonic acid, hexamethaphosphoric acid, tripolyphosphoric acid, orthophosphoric acid, salts of acids above, zinc chloride, acidic zinc chloride, zinc sulfate, zinc ligninsulfonate, and hydrazine.

(b) Scale inhibitor: For example, polyacryric acid, acrylic acid/hydroxyethylidene methacrylate copolymer, acrylic acid/hydroxyethylidene methacrylate/methyl acrylate copolymer, acrylic acid/allylglycidyl ethers copolymer, acrylic acid/2-hydroxy-3-allyloxy-1-propanesulfonic acid copolymer, acrylic acid/isoprenesulfonic acid copolymer, acrylic acid/vinylsulfonic acid copolymer, acrylic acid/allylsulfonic acid copolymer, polymaleic acid, maleic acid or maleic anhydride/isobutylene copolymer, maleic acid or maleic anhydride/styrenesulfonic acid copolymer, maleic acid or maleic anhydride/acrylic acid copolymer, maleic acid or maleic anhydride/acrylate acid copolymer, maleic acid or maleic anhydride/2-acrylamide-2-methylpropanesulfonic acid copolymer, maleic acid or maleic anhydride/amylenic acid copolymer, maleic acid or maleic anhydride/allyl-substituted fluorescent substances (such as 5-allylbenzosuberenol) copolymer, polyacrylamide, polyithaconic acid, and salts of the above substances.

(c) Other antimicrobial agents: For example, halogen- and nitro-substituted aliphatic alcohols (such as 2-bromo-2-nitro-1,3-propanediol; and 2,2-dibromo-2-nitroethanol) and their esters, 2,2-dibromo-3-nitrilopropionamide, alkylene bisthiocyanates (such as methylene bisthiocyanate); 1,4-bisbromoacethoxy-2-butene, hexabromodimethylsulfone, isophthalonitryle type compounds (such as 5-chloro-2,4,6-trifluoroisophthalonitryl and tetrachloroisophthalonitryl), dimethyldithiocarbamate; 4,5-dichloro-1,2-dithiol-3-one; 3,3,4,4-tetrachlorotetrahydrothiophene-1,1-dioxide; tri-iodoallyl alcohol; bromonitrostyrene; aldehyde compounds (such as gluthalaldehyde, phthalaldehyde, isophthalaldehyde, telephthalaldehyde); dichloroglyoxim; benzaldoxim type compounds (such as α-chlorobenzaldoxim acetate and -chlorobenzaldoxim); and 5,5-methylhydantoine.

(d) Antifoaming agent: For example, silicone type or non-silicone type anti-foaming agents.

(e) Algicides: For example, s-triazine type algicide.

Additives are by no means limited to those cited in the above but the other additives can be also used.

The antimicrobial composition of the present invention is prepared according to, for example, a formula in the following using the above mentioned additives.

Formula (by weight %)

| | |
|---|---|
| Isothiazolone type compound: | 0.1–5 |
| Skin irritation suppressor: | 0.1–60 |
| Corrosion inhibitor: | 0–50 |
| Scale inhibitor: | 0–50 |
| Antimicrobial agent: | 0–30 |
| Antifoaming agent: | 0–10 |
| Algicide agent: | 0–10 |
| Solvent (Water, propylene glycol): | 30–99 |

Thus prepared antimicrobial composition of the present invention is added to the systems so that a desired concentration of the isothiazolone type compounds is obtained in the system, which differs according to the purpose as follows:

(i) Anti-slime purpose in a pulp and paper mill system or cooling water system, etc.: isothiazolone type compound concentration of 0.1–25 $g/m^3$.

(ii) Antiseptic purpose in plastic emulsion, starch paste, starch slurry, paint, cutting fluid for metals, etc: isothiazolone type compounds concentration of 0.1–5000 $g/m^3$.

EXAMPLES

The present invention will now be described more specifically in the following by means of the examples and comparative examples, which, however, do not limit the present invention as far as they do not depart from the spirit of the present invention.

The isothiazolone type compounds and other antimicrobial agents used in the examples and comparative examples are as follows:

[Chemicals containing isothiazolone type compounds]

Zonen F: A chemical containing 14 weight % of a mixture of 5-chloro-2-methyl-4-isothiazoline-3-one (Cl-MIT) and 2-methyl-4-isothiazoline-3-one (MIT) together with ethyleneglycol.

Kathon WT: An aqueous solution containing 14 weight % of a mixture of Cl-MIT and MIT together with magnesium chloride and magnesium nitrate.

[Other chemical containing antimicrobial agent]

Dibnirol A-75: A chemical containing 75 weight % of 2,2-dibromo-2-nitroethanol (DBNE) together with diethyleneglycol.

Example 1, Comparative Examples 1, 2

Chemicals were dissolved by stirring according to the compositions shown in Table 1 to prepare the antimicrobial compositions.

TABLE 1

|  | Example 1 | Comparative Example 1 | Comparative Example 2 |
|---|---|---|---|
| Isothiazolone type compound (Zonen F) | 10 | 10 | — |
| Skin irritation suppressor (EBP)* | 12 | — | — |
| Solvent (Propyleneglycol) | 64.6 | 76.6 | 86.6 |
| Other antimicrobial agent (Dibnirol A-75) | 13.4 | 13.4 | 13.4 |

*EBP: 4,4'-ethylidenebisphenol

The prepared antimicrobial compositions were subjected to a skin irritation screening test using each 3 white rabbits (New Zealand white breed). A portion of the normal skin of the rabbit was provided as the test portion which was covered for 4 hours with a gauze patch dipped with 0.5 ml of the non-diluted chemical. After 4 hours the patch was removed, the test portion was washed and the state of the test portion of the skin was observed and recorded at 1, 24, 48, and 72 hours after the washing, according to the following evaluation criteria. In addition, the evaluated score was averaged for 72 hours and indicated as skin primary irritation index (PII).

The obtained results are shown in Table 2.

Evaluation Criteria

| Erythema formation: | |
|---|---|
| No erythema | 0 |
| Very light erythyema (hardly discernible) | 1 |
| Clear erythema | 2 |
| Medium to high degree erythema | 3 |
| High degree erythema to slight skin formation | 4 |
| Edema formation: | |
| No edema | 0 |
| Very light edema (hardly discernible) | 1 |
| Light edema (clear bulge with discernible edge) | 2 |
| Medium edema (about 1 mm bulge) | 3 |

High degree edema (about 1 mm bulge surpassing test portion) 4

TABLE 2

|  | Number | Score development Erythema | | | | Edema | | | | Skin primary irritation index (PII) |
|---|---|---|---|---|---|---|---|---|---|---|
|  |  | 1 | 24 | 48 | 72 Hr | 1 | 24 | 48 | 72 Hr |  |
| Example | 01 | 2 | 2 | 2 | 2 | 4 | 3 | 3 | 2 | 4.8 |
|  | 02 | 2 | 2 | 2 | 2 | 4 | 3 | 2 | 2 |  |
|  | 03 | 2 | 2 | 2 | 2 | 4 | 3 | 2 | 2 |  |
| Comparative Example 1 | 01 | 4 | 4 | 4 | 4 | 4 | 4 | 4 | 4 | 8.0 |
|  | 02 | 4 | 4 | 4 | 4 | 4 | 4 | 4 | 4 |  |
|  | 03 | 4 | 4 | 4 | 4 | 4 | 4 | 4 | 4 |  |
| Comparative Example 2 | 01 | 2 | 2 | 2 | 1 | 4 | 3 | 2 | 1 | 4.3 |
|  | 02 | 2 | 2 | 2 | 1 | 3 | 3 | 2 | 1 |  |
|  | 03 | 2 | 2 | 2 | 2 | 4 | 3 | 2 | 2 |  |

The PII value in the example where EBP is combined together with C1-MIT, MIT and DBNE is 4,8, while the PII value in Comparative Example 1 is 8.0, indicating a very strong skin irritation. From this result, the effect of EBP to decrease the skin irritation is confirmed. Also, it has become clear that the skin irritation of the composition in which EBP is contained is decreased to the level of Comparative Example 2 where only DBNE is used.

A test of antimicrobial activity was performed using the antimicrobial compositions of Example 1 Comparative Example 1.

Bacillus subtillus was inoculated on a liquid culture medium based on peptone-yeast extract (containing peptone 1 g/l and yeast extract 1 g/l) so that a level of $10^6$ bacteria/mL was attained. Then, the antimicrobial compositions of Example 1 and Comparative Example 2 were added respectively so that the C1-MIT concentrations shown in Table 3 were obtained. The growth inhibiting effect was checked after 24 hours of cultivation at 30 under shaking.

TABLE 3

| Example | C1-MIT concentration in the medium (mg/L) | Growth inhibiting effect* |
|---|---|---|
| Example 1 | 0.1 | + |
|  | 0.3 | − |
|  | 0.5 | − |
| Comparative Example 1 | 0.1 | + |
|  | 0.3 | − |
|  | 0.5 | − |

*+ Growth was observed
− Growth was inhibited

The results of Table 3 clearly show that the antimicrobial composition of Example 1 has an growth inhibition effect which is equivalent to the antimicrobial composition of Comparative Example 1.

Examples 2–4, Comparative Examples 3, 4

Chemicals were dissolved by stirring according to the compositions shown in Table 4 to prepare the antimicrobial compositions.

TABLE 4

|  |  | Example | | | Comparative Examples | | (Part in weight) |
|---|---|---|---|---|---|---|---|
|  |  | 2 | 3 | 4 | 3 | 4 |
| Isothiazolone type compounds | Zonen F | 5 | — | 5 | 5 | — |
|  | Kathon | — | 5 | — | — | 5 |

TABLE 4-continued

|  |  | Example | | | Comparative Examples (Part in weight) | |
|---|---|---|---|---|---|---|
|  |  | 2 | 3 | 4 | 3 | 4 |
|  | WT |  |  |  |  |  |
| Skin irritation suppressor (pyromellitic acid) |  | 0.85 | 0.85 | 0.85 | — | — |
| Solvent (water) |  | 94.15 | 94.15 | 73.05 | 95 | 95 |
| Others | Benzotriazole | — | — | 0.1 | — | — |
|  | 2-bromo-2-nitro-1,3-propanediol | — | — | 1.0 | — | — |
|  | Aqueous solution of polymaleic acid type compound (50 weight %) | — | — | 20 | — | — |

The prepared antimicrobial compositions were subjected to a skin irritation screening test in a similar way as in Example 1 to obtain the skin primary irritation index (PII), of which results are shown in Table 5.

TABLE 5

|  | Examples | | | Comparative Examples | |
|---|---|---|---|---|---|
|  | 2 | 3 | 4 | 3 | 4 |
| Skin primary irritation index (PII) | 3.1 | 5.6 | 2.6 | 6.8 | 6.9 |

The results of Table 5 clearly show that the compositions of Examples 2–4 in which pyromellitic acid were combined can decrease the skin irritation in comparison to the composition of Comparative Example 3 containing no pyromellitic acid. It is also shown from the results of Example 2 and Example 3 that the irritation decreasing effect is greater in the composition in which the isothiazolone type compounds do not form a complex with magnesium salts.

Example 5, Comparative Example 5

Chemicals were dissolved by stirring according to the compositions shown in Table 6 to prepare the antimicrobial compositions.

TABLE 6

|  | Example 5 | Comparative Example 5 (Part by weight) |
|---|---|---|
| Isothiazolone type compound (4,5-dichloro-2-octyl-4-isothiazoline-3-one) | 1 | 1 |
| Skin irritation suppressor (4,4'-cyclohexilidenebispbenol) | 1.5 | — |
| Solvent (Propyleneglycol) | 97.5 | 99 |

The prepared antimicrobial compositions were subjected to a skin irritation screening test in a similar way as in Example 1 to obtain the skin primary irritation index (PII), of which results are shown in Table 7.

TABLE 7

|  | Example 5 | Comparative Example 5 |
|---|---|---|
| Skin primary irritation index (PII) | 5.0 | 7.8 |

The results of Table 7 clearly show that the composition of Example 5 in which 4,4'-cyclohexilidenebisphenol was combined can decrease the skin irritation in comparison to the composition of Comparative Example 5 which does not contain 4,4'-cyclohexilidenebisphenol.

Examples 6, 7

Chemicals were dissolved by stirring according to the composition shown in Table 8 to prepare the antimicrobial compositions.

TABLE 8

|  |  | Example (Part by weight) | |
|---|---|---|---|
|  |  | 6 | 7 |
| Isothiazolone type compounds | Zonen F | 5 | 5 |
| Skin irritation suppressor | Oxalic acid (dihydrate) | 0.5 | — |
|  | Trimellitic acid | — | 1.9 |
| Solvent (water) |  | 73.4 | 72.0 |
| Others | Benzotriazole | 0.1 | 0.1 |
|  | 2-bromo-2-nitro-1,3-propanediol | 1.0 | 1.0 |
|  | Aqueous solution of polymaleic acid type compound (50 weight %) | 20 | 20 |

The prepared antimicrobial compositions were subjected to a skin irritation screening test in a similar way as in Example 1 to obtain the skin primary irritation index (PII), of which results are shown in Table 9.

TABLE 9

|  | Example | |
|---|---|---|
|  | 6 | 7 |
| Skin primary irritation index (PII) | 3.7 | 4.0 |

The results of Table 9 show an excellent skin irritation decreasing effect of the compositions 6 and 7 in which oxalic acid or trimellitic acid is combined, respectively.

As is described in detail in the above, the microbial composition of the present invention is a solution type chemical in which the isothiazolone type compounds and those compounds which can form molecular compound therewith are combined. This composition can substantially decrease the skin irritation of the isothiazolone type compounds as a result of molecular compound formation and also by way of assuming the solution form. Since this composition is a solution, it offers no limitation to the injection pump, thus improving the handling and operation properties. In addition, the fact that the isothiazolone type compounds form intermolecular bond with skin irritation suppressor even in the solution state prevents the isothiazolone type compounds from reacting with the other compounds causing deterioration in the antimicrobial activity.

What is claimed is:

1. An antimicrobial method for preventing slime in a pulp and papermaking system comprising a step of adding a composition which contains one or more isothiazolone compounds and a compound for decreasing skin irritation of said isothiazolone compounds in a molar ratio of 1:0.1–1:50 and which is dissolved in a solvent in such a way that a concentration of the isothiazolone compound in the system is from 0.1 to 25 $g/m^3$.

2. The method of claim 1, wherein the compound for decreasing the skin irritation of isothiazolone compounds is dicarboxylic acids, aromatic carboxylic acids, phenolic compounds, or amide compounds.

3. The method of claim 1, wherein the isothiazolone compounds are one or more compounds selected from the group consisting of compounds represented by the following formulas (1) and (2):

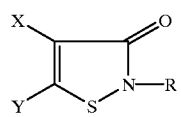
(1)

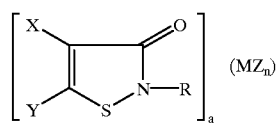
(2)

(In the formulas (1) and (2) shown above, R, X, M, Z, a, and n represent the followings, respectively:

R: Hydrogen atom, alkyl group, alkenyl group, alkynyl group, or aralkyl group;

X: Hydrogen atom or halogen atom;

Y: Hydrogen atom or halogen atom;

M: Cation atom or group selected from a group consisting of alkali metals, alkali earth metals, heavy metals, and amine;

Z: Anion atom or group having a solubility sufficiently high to form a complex with the cation M;

a: An integral number 1 or 2; and n: An integral number with which the anion Z fills the valence of the cation M.).

4. The method of claim 3, wherein the isothiazolone compounds are one or more compounds selected from the group consisting of:

5-chloro-2-methyl-4-isothiazoline-3-one (Cl-MIT); 2-methyl-4-isothiazoline-3-one; 4,5-dichloro-2-methyl-4-isothiazoline-3-one; 2- ethyl-4-isothiazoline-3-one; 2-octyl-4-isothiazoline-3-one; 5-chloro-2-octyl-4-isothiazoline-3-one; 4,5-dichloro-2-octyl-4-isothiazoline-3-one; and 1,2-benzo-isothiazoline-3-one.

5. The method of claim 2, wherein the carboxylic acids are dicarboxylic acids of the following general formula (3) or aromatic carboxylic acids of the following general formula (4):

$$HOOC—R^1—COOH \quad (3)$$

(In the formula (3), $R^1$ represents single bond, alkylen group with 1–4 carbon atoms, alkenylene group with 1–4 carbon atoms, or alkynylene group with 1–4 carbon atoms.)

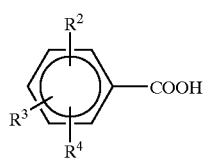
(4)

(In the formula (4), $R^2$, $R^3$, and $R^4$ represent hydrogen, halogen, carboxyl group, hydroxyl group, nitro group, amino group, amide group, and carboxylic anhydride group, as well as alkyl group, alkenyl group, alkynyl group, alkoxy group, alkanone group, or alkanal group each with 1–3 carbon atoms.).

6. The method of claim 2, wherein the carboxylic acids are: oxalic acid; malonic acid; succinic acid; fumaric acid; maleic acid; acetylendicarbonic acid; benzoic acid; phthalic acid; trimellitic acid; pyromellitic acid; 4-nitrobenzoic acid; 4-chloro-3-nitrobenzoic acid; 2-chloro-4-nitrobenzoic acid; 4-chloro-2-nitrobenzoic acid; 2,4-dinitrobenzoic acid; 4-nitrophthalic acid; 3,5-diiodosalicylic acid; 3,5-dinitrosalicylic acid; genticinic acid (2,5-dihydroxybenzoic acid); protocatechuic acid (3,4-dihydroxybenzoic acid); or deoxycholic acid.

7. The method of claim 2, wherein the phenolic compounds are those compounds represented by the following formulas (5), (6) and (7):

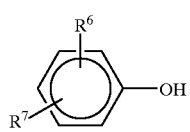
(5)

(In the formula (5), $R^6$ and $R^7$ represent alkyl group with 1–4 carbon atoms.)

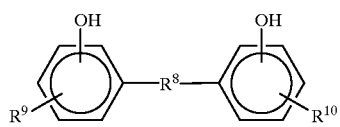
(6)

(In the formula (6), $R^8$ represents methylene group, alkylidene group with 2–4 carbon atoms, cyclohexylidene group, S atom, or $SO_2$ group, and $R^9$, $R^{10}$ represent hydrogen atom or halogen atom.)

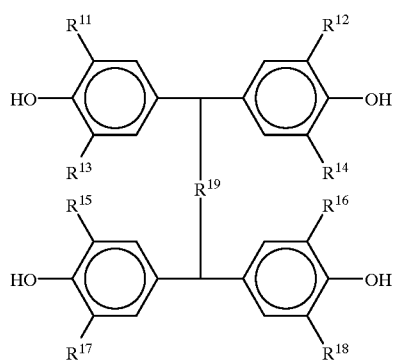

(7)

(In the formula (7), $R^{11}$—$R^{18}$ represent hydrogen atom, alkyl or alkoxy group with 1–3 carbon atoms, or halogen atom, and $R^{19}$ represents single bond, methylene group, ethylene group, or phenylene group.).

8. The method of claim 2, wherein the phenolic compounds are:

2,4-di-t-butylphenol; 2,4-dipropylphenol; 2,2'-methylene-bis(4-chlorophenol); 2,2'-thio-bis(4-chlorophenol); 4,4-cyclohexylidenebisphenol; 4,4'-ethylidenebisphenol; 4,4'-isobutylidenebisphenol; 1,1,2,2-tetrakis(4-hydroxyphenyl)ethane; 1,1,2,2-tetrakis(3-methyl-4-hydroxyphenyl)ethane; 1,1,2,2-tetrakis(3-chloro-4-hydroxyphenyl)ethane; 2,5-di-t-butylhydroquinone; t-butylhydroquinone; 2,5-bis(2,4-dimethylphenyl)hydroquinone; 2,4-dihydroxybenzophenone; 4,4'-dihydroxybenzophenone; 2,2', 4,4'-tetrahydroxybenzophenone; 2-hydroxy-4-methoxybenzophenone; or 1,1'-bi-2-naphtol.

9. The method of claim 2, wherein the amide compound is diphenic bis(dicyclohexylamide).

10. The method of claim 1, wherein the solvent is water and/or hydrophilic organic solvents.

11. The method of claim 10, wherein the hydrophilic organic solvents are one or more solvents selected from the group consisting of:

dimethylformamide, ethyleneglycol, propyleneglycol, diethyleneglycol, dipropyleneglycol, methylcellosolve (ethyleneglycol monomethylether), phenylcellosolve, diethyleneglycol monomethylether, dipropyleneglycol monomethylether, alcohols with carbon atoms up to 8, methyl acetate, ethylacetate, 3-methoxydibutyl acetate, 2-ethoxymethyl acetate, 2-ethoxyethyl acetate, and propylene carbonate.

12. The method of claim 1, wherein the concentration of the isothiazolone compounds in the solution is from 0.1 to 5 weight %.

13. The method of claim 1, wherein the isothiazolone compound and the compound which decreases the skin irritation of the isothiazolone compound are contained in a molar ratio of 1:0.5–1:20 and wherein the concentration of the compound which decreases the skin irritation of the isothiazolone compound is from 0.1 to 20 weight %.

14. The method of claim 1, wherein the composition further contains one or more components selected from the group consisting of corrosion inhibitor, scale inhibitor, antimicrobial agent other than isothiazolone type compounds, antifoaming agent, and algicide.

15. The method of claim 1, wherein the composition is prepared according to the following formula in % by weight:

| | |
|---|---|
| Isothiazolone type compound: | 0.1–5 |
| Skin irritation suppressor: | 0.1–60 |
| Corrosion inhibitor: | 0–50 |
| Scale inhibitor: | 0–50 |
| Antimicrobial agent: | 0–30 |
| Antifoaming agent: | 0–10 |
| Algicide: | 0–10 |
| Solvent: | 30–99. |

16. The method of claim 1, wherein the isothiazolone compound and 4,4'-ethylidenebisphenol are solved in a hydrophilic solvent in which concentration of the isothiazolone compound is 0.1 to 5 wt % and the molar ratio of 4,4'-ethylidenebisphenol to the isothiazolone compound is 1:0.5 to 1:20, the number 1 being for isothiazolone compound.

17. The method of the claim 1, wherein the isothiazolone compound and 4,4-cyclohexylidenebisphenol are solved in a hydrophilic solvent in which concentration of isothiazolone compound is 0.1 to 5 wt % and molar ratio of the 4,4-cyclohexylidenebisphenol to the isothiazolone type compound is 1:0.5 to 1:20, number 1 being for the isothiazolone compound.

18. The composition of the claim 1, wherein the isothiazolone type compound and oxalic acid are solved in a hydrophilic solvent or water in which the concentration of isothiazolone type compound is 0.1 to 5 wt % and the molar ratio of oxalic acid to the isothiazolone type compound is 1:0.5 to 1:20, the number 1 being for the isothiazolone type compound, and at least one of a corrosion inhibitor, a scale inhibitor, another antimicrobial agent than the isothiazolone type compound, an antifoaming agent and an algicide is further solved therein.

19. The composition of the claim 1, wherein the isothiazolone type compound and pyromellitic acid are solved in a hydrophilic solvent or water in which concentration of isothiazolone type compound is 0.1 to 5 wt % and the molar ratio of pyromellitic acid to the isothiazolone type compound is 1:0.5 to 1:20, the number 1 being for the isothiazolone type compound, and at least one of a corrosion inhibitor, a scale inhibitor, another antimicrobial agent than the isothiazolone type compound, and antifoaming agent and an algicide is further solved therein.

20. The composition of the claim 1, wherein the isothiazolone type compound and trimellitic acid are solved in a hydrophilic solvent or water in which the concentration of isothiazolone type compound is 0.1 to 5 wt % and the molar ratio of trimellitic acid to the isothiazolone type compound is 1:0.5 to 1:20, the number 1 being for the isothiazolone type compound, and at least one of a corrosion inhibitor, a scale inhibitor, another antimicrobial agent than the isothiazolone type compound, an antifoaming agent and an algicide is further solved therein.

21. An antiseptic method for a system of plastic emulsion, starch paste, starch slurry, paint and cutting oil for metal, comprising a step of adding a composition which contains one or more isothiazolone compounds and a compound for decreasing skin irritation of said isothiazolone compounds in a molar ratio of 1:0.1–1:50 and which is dissolved in a solvent in such a way that a concentration of the isothiazolone compound in the system is from 1 to 5,000 g/m³.

22. The method of claim 21, wherein the compound for decreasing the skin irritation of isothiazolone compounds is dicarboxylic acids, aromatic carboxylic acids, phenolic compounds or amide compounds.

23. The method of claim 21, wherein the isothiazolone compounds are one or more compounds selected from the group consisting of compounds represented by the following formulas (1) and (2):

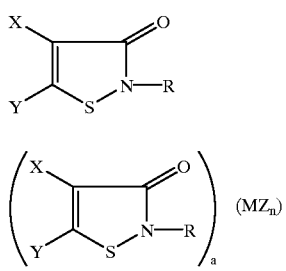

(In the formulas (1) and (2) shown above, R, X, M, Z, a, and n represent the followings, respectively:

R: Hydrogen atom alkyl group, alkenyl group, alkynyl group, or aralkyl group;

X: Hydrogen atom or halogen atom;

Y: Hydrogen atom or halogen atom;

M: Cation atom or group selected from a group consisting of alkali metals, alkali earth metals, heavy metals, and amine;

Z: Anion atom or group having a solubility sufficiently high to form a complex with the cation M;

a: An integral number 1 or 2; and n: An integral number with which the anion Z fills the valence of the cation M.).

24. The method of claim 23, wherein the isothiazolone compounds are one or more compounds selected from the group consisting of:

5-chloro-2-methyl-4-isothiazoline-3-one (C1-MIT); 2-methyl-4-isothiazoline-3-one; 4,5-dichloro-2-methyl-4-isothiazoline-3-one; 2-ethyl-4-isothiazoline-3-one; 2-octyl-4-isothiazoline-3-one; 5-chloro-2-octyl-4-isothiazoline-3-one; 4,5-dichloro-2-octyl-4-isothiazoline-3-one; and 1,2-benzo-isothiazoline-3-one.

25. The method of claim 22, wherein the carboxylic acids are dicarboxylic acids of the following general formula (3) or aromatic carboxylic acids of the following general formula (4):

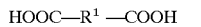

(In the formula (3), $R^1$ represents single bond, alkylen group with 1–4 carbon atoms, alkenylene group with 1–4 carbon atoms, or alkynylene group with 1–4 carbon atoms.)

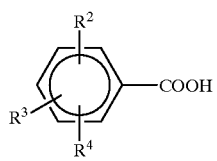

(In the formula (4), $R^2$, $R^3$, and $R^4$ represent hydrogen, halogen, carboxyl group, hydroxyl group, nitro group, amino group, amide group, and carboxylic anhydride group, as well as alkyl group, alkenyl group, alkynyl group, alkoxy group, alkanone group, or alkanal group each with 1–3 carbon atoms.).

26. The method of claim 22, wherein the carboxylic acids are:

oxalic acid; malonic acid; succinic acid; fumaric acid; maleic acid; acetylendicarbonic acid; benzoic acid; phthalic acid; trimellitic acid; pyromellitic acid; 4-nitrobenzoic acid; 4-chloro-3-nitrobenzoic acid; 2-chloro-4-nitrobenzoic acid; 4-chloro-2-nitrobenzoic acid; 2,4-dinitrobenzoic acid; 4-nitrophthalic acid; 3,5-diiodosalicylic acid; 3,5-dinitrosalicylic acid; genticinic acid (2,5-dihydroxybenzoic acid); protocatechuic acid (3,4-dihydroxybenzoic acid); or deoxycholic acid.

27. The method of claim 22, wherein the phenolic compounds are those compounds represented by the following formulas (5), (6) and (7):

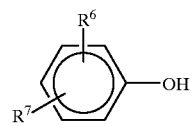

(In the formula (5), $R^6$ and $R^7$ represent alkyl group with 1–4 carbon atoms.)

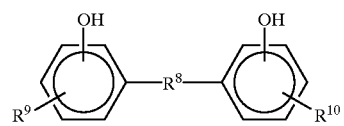

(In the formula (6), $R^8$ represents methylene group, alkylidene group with 2–4 carbon atoms, cyclohexylidene group, S atom, or $SO_2$ group, and $R^9$, $R^{10}$ represent hydrogen atom or halogen atom.)

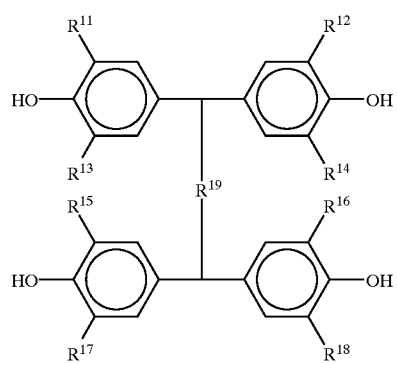

(In the formula (7), $R^{11}$—$R^{18}$ represent hydrogen atom, alkyl or alkoxy group with 1–3 carbon atoms, or halogen atom, and $R^{19}$ represents single bond, methylene group, ethylene group, or phenylene group.).

28. The method of claim 22, wherein the phenolic compounds are: 2,4-di-t-butylphenol; 2,4-dipropylphenol; 2,2'-methylene-bis(4-chlorophenol); 2,2'-thio-bis(4- chlorophenol); 4,4-cyclohexylidenebisphenol; 4,4'-ethylidenebisphenol; 4,4'-isobutylidenebisphenol; 1,1,2,2-tetrakis(4-hydroxyphenyl)ethane; 1,1,2,2-tetrakis(3-methyl-4-hydroxyphenyl)ethane; 1,1,2,2-tetrakis(3-chloro-4-hydroxyphenyl)ethane; 2,5-di-t-butylhydroquinone; t-butylhydroquinone; 2,5-bis(2,4-dimethylphenyl) hydroquinone; 2,4-dihydroxybenzophenone; 4,4'-dihydroxybenzophenone; 2,2',4,4'-tetrahydroxybenzophenone; 2-hydroxy-4-methoxybenzophenone; or 1,1'-bi-2-naphtol.

29. The method of claim 22, wherein the amide compound is diphenic bis(dicyclohexylamide).

30. The method of claim 21, wherein the solvent is water and/or hydrophilic organic solvents.

31. The method of claim 30, wherein the hydrophilic organic solvents are one or more solvents selected from the group consisting of:

dimethylformamide, ethyleneglycol, propyleneglycol, diethyleneglycol, dipropyleneglycol, methylcellosolve (ethyleneglycol monomethylether), phenylcellosolve, diethyleneglycol monomethylether, dipropyleneglycol monomethylether, alcohols with carbon atoms up to 8, methyl acetate, ethylacetate, 3-methoxydibutyl acetate, 2-ethoxymethyl acetate, 2-ethoxyethyl acetate, and propylene carbonate.

32. The method of claim 21, wherein the concentration of the isothiazolone compounds in the solution is from 0.1 to 5 weight %.

33. The method of claim 21, wherein the isothiazolone compound and the compound which decreases the skin irritation of the isothiazolone compound are contained in a molar ratio of 1:0.5–1:20 and wherein the concentration of the compound which decreases the skin irritation of the isothiazolone compound is from 0.1 to 20 weight %.

34. The method of claim 21, wherein the composition further contains one or more components selected from the group consisting of corrosion inhibitor, scale inhibitor, antimicrobial agent other than isothiazolone type compounds, antifoaming agent, and algicide.

35. The method of claim 21, wherein the composition is prepared according to the following formula in % by weight:

| | |
|---|---|
| Isothiazolone type compound: | 0.1–5 |
| Skin irritation suppressor: | 0.1–60 |
| Corrosion inhibitor: | 0–50 |
| Scale inhibitor: | 0–50 |
| Antimicrobial agent: | 0–30 |
| Antifoaming agent: | 0–10 |
| Algicide: | 0–10 |
| Solvent: | 30–99. |

36. The method of claim 21, wherein the isothiazolone compound and 4,4'-ethylidenebisphenol are solved in a hydrophilic solvent in which concentration of the isothiazolone compound is 0.1 to 5 wt % and molar ratio of 4,4'-ethylidenebisphenol to the isothiazolone compound is 1:0.5 to 1:20, number 1 being for the isothiazolone compound.

37. The method of claim 21, wherein the isothiazolone compound and 4,4-cyclohexylidenebisphenol are solved in a hydrophilic solvent in which concentration of the isothiazolone compound is 0.1 to 5 wt % and molar ratio of 4,4-cyclohexylidenebisphenol to the isothiazolone compound is 1:0.5 to 1:20, number 1 being for the isothiazolone compound.

38. The method of claim 21, wherein the isothiazolone compound and oxalic acid are solved in a hydrophilic solvent or water in which concentration of the isothiazolone compound is 0.1 to 5 wt % and molar ratio of oxalic acid to the isothiazolone compound is 1:0.5 to 1:20, number 1 being for the isothiazolone compound, and at least one of a corrosion inhibitor, a scale inhibitor, an antimicrobial agent other than the isothiazolone compound, an antifoaming agent and an algicide is further solved therein.

39. The method of claim 21, wherein the isothiazolone compound and pyromellitic acid are solved in a hydrophilic solvent or water in which concentration of the isothiazolone compound is 0.1 to 5 wt % and molar ratio of pyromellitic acid to the isothiazolone compound is 1:0.5 to 1:20, number 1 being for the isothiazolone compound, and at least one of a corrosion inhibitor, a scale inhibitor, an antimicrobial agent other than the isothiazolone compound, an antifoaming agent and an algicide is further solved therein.

40. The method of claim 21, wherein the isothiazolone compound and trimellitic acid are solved in a hydrophilic solvent or water in which concentration of the isothiazolone compound is 0.1 to 5 wt % and molar ratio of trimellitic acid to the isothiazolone compound is 1:0.5 to 1:20, number 1 being for the isothiazolone compound, and at least one of a corrosion inhibitor, a scale inhibitor, an antimicrobial agent other than the isothiazolone compound, an antifoaming agent and an algicide is further solved therein.

* * * * *